United States Patent
Friedman et al.

(10) Patent No.: US 7,384,579 B2
(45) Date of Patent: Jun. 10, 2008

(54) AQUEOUS SUSPENSIONS OF PENTABROMOBENZYL ACRYLATE

(75) Inventors: Gad Friedman, Rehovot (IL); Emanuel Buchbinder, Kefar Saba (IL); Nurit Kornberg, Lehavim (IL)

(73) Assignee: Bromine Compounds Ltd. (IL)

( * ) Notice: Subject to any disclaimer, the term of this patent is extended or adjusted under 35 U.S.C. 154(b) by 325 days.

(21) Appl. No.: 11/075,054

(22) Filed: Mar. 8, 2005

(65) Prior Publication Data

US 2005/0148788 A1 Jul. 7, 2005

Related U.S. Application Data

(62) Division of application No. 09/878,802, filed on Jun. 11, 2001, now Pat. No. 6,872,332.

(30) Foreign Application Priority Data

Jun. 12, 2000 (IL) .................... 136725

(51) Int. Cl.
*C09K 21/08* (2006.01)
(52) U.S. Cl. ............. 252/610; 252/601; 252/608
(58) Field of Classification Search ......... 252/610, 252/601, 608; 516/77
See application file for complete search history.

(56) References Cited

U.S. PATENT DOCUMENTS

| | | | |
|---|---|---|---|
| 2,662,061 A | 12/1953 | Gilcrease et al. | |
| 3,989,661 A | 11/1976 | Bondy | |
| 4,027,049 A | 5/1977 | Masuda et al. | |
| 4,033,965 A | 7/1977 | Burdeska et al. | |
| 4,128,709 A | 12/1978 | Vollkommer et al. | |
| 4,211,730 A | 7/1980 | Vollkommer et al. | |
| 4,385,164 A | 5/1983 | Sinclair et al. | |
| 4,623,583 A | 11/1986 | Mischutin | |
| 4,632,583 A * | 12/1986 | Nash ............ | 400/248 |
| 4,687,594 A | 8/1987 | Lietz et al. | |
| 4,741,865 A | 5/1988 | Kintz et al. | |
| 4,822,524 A | 4/1989 | Strickland | |
| 4,996,276 A | 2/1991 | Fishler et al. | |
| 5,072,028 A | 12/1991 | Fishler et al. | |
| 5,078,918 A * | 1/1992 | Fishler et al. ........ | 252/609 |
| 5,290,636 A | 3/1994 | Rose et al. | |
| 5,509,940 A | 4/1996 | Zbar et al. | |
| 5,576,366 A * | 11/1996 | Sheth ........... | 524/140 |
| 5,629,378 A | 5/1997 | Takada | |
| 5,948,323 A | 9/1999 | McLaughlin et al. | |
| 6,190,581 B1 | 2/2001 | Duffin, Jr. et al. | |

FOREIGN PATENT DOCUMENTS

| | | |
|---|---|---|
| EP | 0548839 | 6/1993 |
| GB | 2018750 | 10/1979 |
| JP | 4136269 | 5/1992 |

* cited by examiner

*Primary Examiner*—Lorna M. Douyon
*Assistant Examiner*—Amina Khan
(74) *Attorney, Agent, or Firm*—Lerner, David, Littenberg, Krumholz & Mentlik, LLP

(57) ABSTRACT

Pentabromobenzyl acrylate (PBBMA), a useful flame retardant insoluble in water, is provided as an aqueous fluid for industrial applications. The fluid is an easy to handle, stable suspension of finely ground PBBMA in water.

10 Claims, No Drawings

AQUEOUS SUSPENSIONS OF PENTABROMOBENZYL ACRYLATE

CROSS-REFERENCE TO RELATED APPLICATIONS

The present application is a divisional of U.S. application Ser. No. 09/878,802 entitled AQUEOUS SUSPENSIONS OF PENTABROMOBENZYL ACRYLATE, filed Jun. 11, 2001, now U.S. Pat. No. 6,872,332 which claims foreign priority on Israeli Application No. 136725, filed on Jun. 12, 2000, the disclosures of which are incorporated herein by reference.

FIELD OF THE INVENTION

This invention relates to novel compositions of matter that are aqueous suspensions of pentabromobenzyl acrylate (PBBMA) and to a process for making them.

BACKGROUND OF THE INVENTION

Pentabromobenzyl acrylate (PBBMA) is an acrylic monomer, which is useful in many applications, especially but not exclusively, in the field of fire retardants for plastic compositions. It can be polymerized easily by known techniques such as bulk polymerization, solution polymerization etc., or by mechanical compounding or extrusion. In mechanical compounding or extrusion, it may be grafted onto existing polymer backbones, or added to unsaturated loci on polymers.

All these properties render PBBMA a particularly useful tool in the hands of experienced compounders. However, it has been impossible, so far, to carry out aqueous manipulations with PBBMA, in spite of their desirability, because, on the one hand, PBBMA is insoluble in water, and on the other hand, because of its high bromine content, it has a high specific gravity, about 2.7, —and therefore does not lend itself to the preparation and use of aqueous suspensions.

It is a purpose of this invention to provide stable dispersions or suspensions of PBBMA, which are new compositions of matter. Dispersions and suspensions are to be considered synonyms, as used herein.

It is another purpose of this invention to provide such dispersions or suspensions that are aqueous dispersions or suspensions.

It is a further purpose of this invention to provide a process for preparing such suspensions.

It is a further purpose of this invention to provide suspensions of PBBMA for particular applications in industry.

It is a still further purpose of this invention to provide suspensions of PBBMA together with additional compounds, such as synergists for increasing the fire-retarding efficiency of compositions obtained from PBBMA.

It is a still further purpose of this invention to provide processes comprising the polymerization and/or copolymerization of PBBMA for the production of particular products.

Other purposes and advantages of the invention will appear as the description proceeds.

SUMMARY OF THE INVENTION

The suspension of PBBMA, according to the invention, is characterized in that it comprises PBBMA in the form of finely ground particles, having a size smaller than 50 μm and preferably smaller than 10 μm and more preferably from 0.3 μm to 10 μm, and contains suspending agents chosen from among xanthene gums, anionic or nonionic purified, sodium modified montmorilonite, naphthalene sulfonic acid-formaldehyde condensate sodium salt, sodium or calcium or ammonium salts of sulfonated lignin, acrylic acids/acrylic acids ester copolymer neutralized—sodium polycarboxyl, and wetting agents chosen from among alkyl ether, alkylaryl ether, fatty acid diester and sorbitan monoester types, polyoxyethylene (POE) compounds. The POE compounds are preferably chosen from among:
POE allyl ethers N—5; 10; 20;
POE lauryl ethers N—5; 10; 20;
POE acetylphenyl ethers N—3; 5; 10; 20;
POE nonylphenyl ethers N—3; 4; 5; 6; 7; 10; 12; 15; 20;
POE dinonylphenyl ethers N—5; 10; 20;
POE oleate—N—9, 18, 36;
Sorbitan monooleate N—3; 5; 10; 20.
Alkyl naphthalene sulfonates or their sodium salts.
N is the number of ethylene oxide units.

Said suspension is typically, though not necessarily, an aqueous one.

The suspension according to the invention may also include nonionic or anionic surface active agents or wetting agents, which can be chosen by persons skilled in the art. For example, nonionic agents may be polyoxyethylene (POE) alkyl ether type, preferably NP-6 (Nonylphenol ethoxylate, 6 ethyleneoxide units). Anionic agents may be free acids or organic phosphate esters or the dioctyl ester of sodium sulfosuccinic acid. It may, also, include other additives which function both as dispersing agents and suspending agents commonly used by skilled persons like sodium or calcium or ammonium salts of sulfonated lignin, acrylic acids/acrylic acids ester copolymer neutralized—sodium polycarboxyl, preferably naphthalene sulfonic acid—formaldehyde condensate sodium salt. The suspension according to the invention may also include defoaming or antifoaming agents, which can be chosen by persons skilled in the art. For example, emulsion of mineral oils or emulsion of natural oils or preferably emulsion of silicon oils like AF-52™.

The invention further comprises a method of preparing a suspension of PBBMA, which comprises grinding the PBBMA together with wetting agent and preferably also dispersing agent to the desired particle size adding it to the suspending medium, consisting of water containing suspension stabilizing agents, with slow stirring, preferably at 40 to 400 rpm. Grinding is preferably carried out with simultaneous cooling. The order of the addition of the wetting agents, the dispersing agents and the suspending agents is important.

Preserving or stabilizing agents such as Formaldehyde, and preferably a mixture of methyl and propyl hydroxy benzoates, can also be added to the suspension.

Typical size distributions of PBBMA both before grinding and as they are when present in suspensions according to the invention, are listed hereinafter. "D" indicates the diameter of the particles in μm and S.A. indicates the surface area in square meters per gram. "v" designates volume and 0.25 means 25% by volume.

|  | D(v, 0.1) | D(v, 0.5) | D(v, 0.9) | Specific S.A. |
|---|---|---|---|---|
| PBBMA before grinding | 2.40 | 19.34 | 58.20 | 0.3623 |
| PBBMA in Suspension | 0.36 | 1.54 | 6.62 | 2.2554 |

In an embodiment of the process of the invention, wherein suspensions of PBBMA and additional compounds—such as fire-retardant synergists, e.g. fire-retardant antimony oxide (AO), the process comprises preparing a suspension of the additional compound in a way similar to the preparation of the PBBMA suspension, and then mixing the two suspensions, preferably by adding the suspension of the additional compound to a slowly stirred suspension of PBBMA, and continuing stirring until a homogeneous, mixed suspension is obtained.

The suspensions, in particular the aqueous suspensions, of the invention are stable. When stored at room temperature, they are stable for at least two weeks and preferably at least one month. Their stability may be higher, e.g. three months or more. If they have to be stored at high temperature, they should pass the "Tropical Storage Test", at 54° C., viz. be stable under such Test for at least one week.

DETAILED DESCRIPTION OF PREFERRED EMBODIMENTS

The following examples are intended to illustrate the invention, but are not binding or limitative.

EXAMPLE 1

Preparation of a Suspension of PBBMA

A glass bead wet mill equipped with cooling jacket and continuous feed by a peristaltic pump, was utilized for grinding. PBBMA (750 gr) was mixed with water (240 ml), NP-6 (Nonylphenol ethoxylate) (1 ml) and Darvan#1 (Naphtalenesulfonic acid formaldehyde condensate, sodium salt) (30 gr). The mixture was fed into the grinding beads mill over a period of 25 min. The resulting slurry was stirred gently, mechanical blade stirrer, 40-60 rpm, and 10 ml of 1.5% Rhodopol 23, Xanthan Gum (CAS No 11138-66-2) in water with preserving agents, 1% Methyl Paraben,methyl-4-hydroxybenzoate, CAS No 99-76-3 and 0.5% Propyl Paraben, propyl-4-hydroxybenzoate, CAS No 94-13-3, were added.

EXAMPLE 2

Preparation of a PBBMA-AO Suspension

A suspension of Antimony Oxide was prepared as follows. To a 3-liter round bottom flask, fitted with a mechanical stirrer, were added water (240 ml), NP-6 (1 ml) (Nonylphenol ethoxylate), and Darvan #1 (Naphtalenesulfonic acid formaldehyde condensate, sodium salt) (30 g). Finely ground antimony oxide, Ultrafine grade with typical average particle size of 0.2 μm-0.4 μm. (AO, 750 g) was slowly added under fast stirring, 400-600 rpm. The stirrer was slowed, 50-150 rpm and a 1.5% solution of Rhodopol 23 Xanthan Gum (CAS No 11138-66-2) with preserving agents—1% Methyl Paraben,methyl-4-hydroxybenzoate, (CAS No 99-76-3) and 0.5% Propyl Paraben, propyl-4-hydroxybenzoate, (CAS No 94-13-3) were added (115 ml).

The mixed PBBMA-AO suspension was prepared as follows. To a slowly stirred, 40 rpm, suspension of PBBMA (750 ml) at 25° C.-30° C., obtained as described in Example 1, was added the AO suspension (250 ml) as described above. After five minutes, stirring was stopped, yielding a homogeneous mixture.

EXAMPLE 3

Preparation of a PBBMA-Styrene-Butylacrylate Terpolymer Latex

In a 0.5 L 4 necked round bottom flask fitted with mechanical stirrer, reflux condenser, thermometer, dropping funnel and Nitrogen inlet were charged 1.4 gr SDS (Sodium Dodecyl Sulfate) and 100 mL of water. The flask was immersed in an oil bath and heated to 70° C. with continuous stirring, 250 rpm, Nitrogen was introduced under the surface of the liquid. After 1 hr. the nitrogen inlet was raised above the surface of the liquid and 0.15 gr of $K_2S_2O_8$ were added. 5 min. later a solution of 15 gr Styrene and 15 gr Butylacrylate was added dropwise over 30 min. The emulsion pre-polymerization was continued for another 90 min. after which 6 gr of a PBBMA suspension (~60% solids) were added dropwise over 70 min. The polymerization was continued overnight.

A stable latex (stable for more than two month) was obtained.

The terpolymer isolated from this emulsion was characterized. The bromine content was 7% and the glass transition temperature was 18.8° C.

EXAMPLE 4

Preparation of a PBBMA-Styrene-Acrylonitrile Terpolymer

In a 0.5 L 4 necked round bottom flask fitted with mechanical stirrer, reflux condenser, thermometer, dropping funnel and Nitrogen inlet were charged 1.4 gr SDS (Sodium Dodecyl Sulfate) and 100 mL of water. The flask was immersed in an oil bath and heated to 70° C. with continuous stirring, 250 rpm, Nitrogen was introduced under the surface of the liquid. After 1 hr. the nitrogen inlet was raised above the surface of the liquid and 0.15 gr of $K_2S_2O_8$ were added. 5 min. later a solution of 18.2 gr Styrene and 5.8 gr Acrylonitrile was added dropwise over 30 min. The emulsion pre-polymerization was continued for another 20 min. after which 8.5 gr of a PBBMA suspension (~60% solids) were added dropwise over 40 min. A second portion of 0.15 gr of $K_2S_2O_8$ was added 3 hr. after the addition of the suspension was finished. The polymerization was continued overnight.

A stable latex (stable for at least one month) was obtained.

The terpolymer isolated from this emulsion was characterized. The bromine content was 12.5%, the nitrogen content was 5% and the glass transition temperature was 107° C. The molecular weight depends on the polymerization conditions. In this particular case a Weight Average Molecular Weight, Mw, of $1.2*10^6$ and Number Average Molecular Weight, Mn, of 422,000, was determined (in Dimethylformamide solution, calibrated with Polystyrene standards).

The suspensions of the invention are useful for a number of applications, and the way in which they are used and the resulting products, are also part of the invention.

Fire Retardants are commonly used in carpet-backings However, the fire retardants of the prior art are not bound to the carpet, and are susceptible to removal by dry cleaning. According to the invention, the aqueous suspension of PBBMA is applied to the reverse side of the carpets and is polymerized by heating at temperatures above 130° C. This results in a coating of PBBMA polymer which is bound to the carpet.

In the prior art, fire retardants are used in the textile industry. However, they generally produce light scattering, because they are used in powder form. According to the invention, the aqueous solution of PBBMA, optionally with complementary components, is applied to textile materials and penetrates into the fibers, and then polymerization is effected by heating at temperatures above 130° C., thus polymerizing PBBMA and binding the resulting polymers to the fibers. Addition of free radical initiating catalysts, the conventional polymerization catalysts such as organic peroxides, e.g., benzoylperoxide, or other free radical producing catalysts, e.g., azobisisobutyronitrile, will shorten polymerization time.

The PBBMA suspensions of the invention can be used to copolymerize PBBMA with other monomers or grafted to polymers, in order to produce adhesives which are also fire-retardants or other types of surface modifiers and binding promoters.

Likewise, the suspensions of the invention can be used to copolymerize PBBMA with other (meth)acrylate derivatives, such as butyl acrylate, methyl methacrylate or other monomers, to produce transparent plastics of predetermined refraction indices.

Double layered particles can also be produced, according to the invention, by adding another monomer, e.g. another (meth)acrylic derivative, to the PBBMA suspensions under polymerization conditions, to produce very stable latexes. An example of such other monomers can be, for instance, aliphatic (meth)acrylates or hydroxyethyl acrylate.

The novel products obtained according to the invention, and the processes for their production, are also part of the invention.

While examples of the invention have been described for purposes of illustration, it will be apparent that many modifications, variations and adaptations can be carried out by persons skilled in the art, without exceeding the scope of the claims.

The invention claimed is:

1. A suspension of pentabromobenzyl acrylate (PBBMA), comprising PBBMA in the form of finely ground particles having a size smaller than 50 µm and containing a suspending agent selected from the group consisting of xanthene gums, anionic or nonionic purified sodium modified montmorilonite, naphthalene sulfonic acid-formaldehyde condensate sodium salt, sodium, calcium or ammonium salts of sulfonated lignin, and acrylic acids/acrylic acids ester copolymer neutralized—sodium salt, and further a wetting agent selected from the group consisting of alkyl ether, alkylaryl ether, fatty acid diester or monoester of sorbitan, and polyoxyethylene (POE) compounds.

2. A suspension according to claim 1, wherein said wetting agent is selected from the group consisting of:
POE allyl ethers N—5; 10; 20;
POE lauryl ethers N—5; 10; 20;
POE acetylphenyl ethers N—3; 5; 10; 20;
POE nonylphenyl ethers N—3; 4; 5; 6; 7; 10; 12; 15; 20;
POE dinonylphenyl ethers N—5; 10; 20;
POE oleate N—9, 18, 36;
sorbitan monooleate N—3; 5; 10; 20; and
alkyl naphthalene sulfonates or their sodium salts;
wherein N is the number of ethylene oxide units.

3. A suspension according to claim 1, wherein said suspending medium is water.

4. A suspension according to claim 1, wherein said PBBMA is in the form of particles having a size from 0.3 µm to 10 µm.

5. A suspension according to claim 1, wherein said suspension comprises an aqueous suspension, and said suspending agent comprises xanthene gums.

6. A suspension according to claim 1, wherein said suspension comprises an aqueous suspension, and said suspension has a stability at room temperature of at least two weeks.

7. A suspension according to claim 1, wherein said suspension comprises an aqueous suspension, and said suspension has a stability at room temperature of at least one month.

8. A suspension according to claim 1, wherein said suspension comprises an aqueous suspension, and said suspension has a stability of at least one week according to the "Tropical Storage Test", at 54° C.

9. A suspension according to claim 1, wherein said suspension comprises an aqueous suspension, and said suspension further comprises a nonionic or anionic surface active agent.

10. A suspension according to claim 9, wherein said surface active agent is selected from the group consisting of polyalkylene glycol ethers, free acids, organic phosphate esters, the dioctyl ester of sodium sulfosuccinic acid, and polyoxyethylene alkyl ethers.

* * * * *